(12) United States Patent
Yoon et al.

(10) Patent No.: US 6,753,430 B2
(45) Date of Patent: Jun. 22, 2004

(54) OPTICALLY ACTIVE QUINOLINE CARBOXYLIC ACID DERIVATIVES WITH 7-PYRROLIDINE SUBSTITUENTS CAUSING OPTICAL ACTIVITY AND A PROCESS FOR THE PREPARATION THEREOF

(75) Inventors: Sung June Yoon, Seoul (KR); Yong Ho Chung, Anyang-si (KR); Chi Woo Lee, Koonpo-si (KR); Jin Soo Lee, Anyarg-si (KR); Nam Doo Kim, Inchon-si (KR); Yoon Ho Jin, Seoul (KR); Wan Jin Song, Seoul (KR); Ik Hoe Kim, Suwon-si (KR); Wang Yong Yang, Kyunggi-do (KR); Dong Rack Choi, Koonpo-si (KR); Jung Han Shin, Suwon-si (KR)

(73) Assignee: Dong Wha Pharm. Ind. Co., Ltd (KR)

( * ) Notice: Subject to any disclaimer, the term of this patent is extended or adjusted under 35 U.S.C. 154(b) by 4 days.

(21) Appl. No.: 10/600,631

(22) Filed: Jun. 20, 2003

(65) Prior Publication Data

US 2004/0029915 A1 Feb. 12, 2004

Related U.S. Application Data

(62) Division of application No. 09/979,644, filed on Nov. 16, 2001, now Pat. No. 6,649,763.

(30) Foreign Application Priority Data

May 20, 1999 (KR) ............................................ 11-18158
May 9, 2000 (KR) ......................................... 2000-24657
May 18, 2000 (KR) .............................. PCT/KR00/00487

(51) Int. Cl.$^7$ ............................................ C07D 471/02
(52) U.S. Cl. ...................................... 546/123; 546/122
(58) Field of Search ................................ 546/122, 123

(56) References Cited

U.S. PATENT DOCUMENTS 5,276,041 A * 1/1994 Nakano et al. ............ 514/314
5,633,262 A * 5/1997 Hong et al. ................ 514/300

FOREIGN PATENT DOCUMENTS

EP 0 688 772 A1 6/1995
EP 0 688 771 A1 * 12/1995
WO WO 99/00393 * 1/1999

OTHER PUBLICATIONS

Hyun et al II, "Separation of the storeoisoncals, etc" CA 134: 33088 (2000).*
Hyun et al II, "Liquid chromatographic resolution, etc" CA 134: 65629 (2000).*
Hyun, J Luq Chrom & Rel Techno., vol 23(17), 2669–2682, 2000.*
Hyun, CA 134:33080, 2000.*
Hyun, CA 134:65629, 2000.*
Hong, C.Y., et al, "Novel Fluorequinolone Antibacterial Agents Containing Ontime–Substituted (Aminomethyl) pyrrilodines: Synthesis and Antibacterial Activity of 7–(Aminomethyl)–3–(methotyimine)pyrrolidin–1–yl)–1–cycloprophyl–6–fluoro–4–oxo–1, 4–dihydro[1,8] naphthyridine–3–carboxylic Acid (LB20304)", J. Med. Chem., 1997, vol. 40, pp. 3584–3593.
Chu, D.T.W., et al "Synthesis Antibacterial Activities and Pharmacological Properties of Enantiometers of Temsfloxacin Hydrochloride", J. Med. Chem., 1991, vol. 34, pp. 168–174.
Stinson, S.C., "Counting on Chiral Drugs", C&EN, Sep. 21, 1998, pp. 83–104.

* cited by examiner

Primary Examiner—D. Margaret Seaman
(74) Attorney, Agent, or Firm—Muserlian, Lucas & Mercanti, LLP

(57) ABSTRACT

The present invention relates to optically active quinoline carboxylic acid derivatives, their pharmaceutically acceptable salts, their solvates, and a process for the preparation thereof. More specifically, the present invention relates to optically active quinoline carboxylic acid derivatives containing 4-aminomethyl-4methyl-3-(Z)-alkoxyiminopyrrolidine substituents causing optical activity at the 7-position of the quinolone nuclei. As the compounds of the present invention have superior antibacterial activity and pharmacokinetic profiles to their enantiomers, their racemates and conventional antibacterial agents, with nearly no phototoxicity, the compounds of this invention are useful for antibacterial agents.

5 Claims, No Drawings

OPTICALLY ACTIVE QUINOLINE CARBOXYLIC ACID DERIVATIVES WITH 7-PYRROLIDINE SUBSTITUENTS CAUSING OPTICAL ACTIVITY AND A PROCESS FOR THE PREPARATION THEREOF

This patent application is a divisional of U.S. patent application Ser. No. 09/979,644, filed on Nov. 16, 2001, now U.S. Pat. No. 6,649,763, which claims a benefit of priority from Korean Patent Application No. 1999/18158 filed May 20, 1999 and Korean Patent Application No. 2000/24657 filed May 9, 2000, through PCT Application Serial No. PCT/KR00/00487, the contents of each of which are incorporated herein by reference.

TECHNICAL FIELD

The present invention relates to optically active quinoline carboxylic acid derivatives represented by following formula 1, their pharmaceutically acceptable salts, their solvates, and a process for the preparation thereof. More specifically, the present invention relates to optically active quinoline carboxylic acid derivatives containing 4-aminomethyl-4-methyl-3-(Z)-alkoxyimino pyrrolidine substituents at 7-position of the quinolone nuclei.

Formula 1

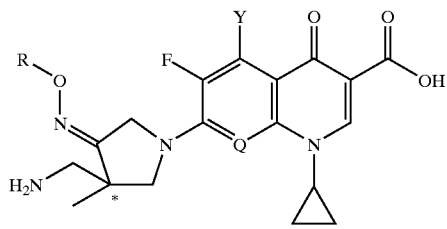

Wherein

Q is C—H, C—F, C—Cl, or N;

Y is H, or $NH_2$;

R is a straight or branched alkyl group of $C_1$–$C_4$, an allyl group, or a benzyl group; and

* represents optically pure chiral carbon atom.

BACKGROUND ART

Quinolone antibacterial agents show high therapeutic efficacy even when being administered orally as well as can be made available for parenteral dosage forms. At present, quinolone antibacterial agents are prevalently used to treat the diseases caused by bacterial infection. In general, quinolone antibacterial agents are classified into three generations according to chemical structure, activity and pharmacokinetics (David C. Hooper and John S. Wolfson. Quinolone Antibacterial Agents; American Society for Microbiology: Washington D.C., 1993: pp 1–2). The first-generation quinolone antibacterial agents were usually used for the treatment of urinary tract infection and were restricted to the treatment of the diseases caused by Gram-negative bacteria. It was riot until the second-generation emerged that quinolone antibacterial agents could be come to exert their activities against some Gram-positive pathogens as well as Gram-negative pathogens. The second-generation quinolone antibacterial agents were also greatly improved in the pharmacokinetics of absorption and distribution. The third-generation quinolones, which have been recently developed, can be administered as once daily dosing form because of long half life in case of lomefloxacin and fleroxacin, and show excellent pharmacokinetics and highly potent activity against Gram-positive bacteria in case of sparfloxacin, trovafloxacin, moxifloxacin and gatifloxacin. However, these conventional quinolone antibacterial agents are still weakly potent against the repression of streptococci and enterococci and quinolone-resistant strains are increasingly generated.

Most of conventional quinolone antibacterial agents have piperazine derivatives substituted at the 7-position but it was known that pyrrolidine derivatives were introduced into the 7-position in order to enhance the antibacterial activity against Gram-positive strains (Sanchez, J. P., et al., *J. Med. Chem.*, 31, 983 (1988)). The quinolone antibacterial agents in which pyrrolidine derivatives are substituted at the 7-position were certainly improved in the antibacterial activity against Gram-positive strains, but suffered from a problem in that the in vivo antibacterial activity did not correspondently reflected in vitro activity because of their poor water solubility and pharmacokinetic profiles.

Introduction of halogens into quinolone antibacterial agents at the 8-position is known to increase their antibacterial activity, but also to generate phototoxicity (Sanchez, J., et al., *J. Med. Chem.*, 35, 361–367 (1992)).

Korean Pat. No. 174,373 discloses a racemate which corresponds to the compound to be targeted in the present invention. However, its optical isomers, that is, isomers with pure (+) or (−) optical activity are not described. Nowhere are mentioned preparation or separation methods of the optical isomers. Neither are pharmacological effects of each isomer taken into account, nor is a description given of the relation between the racemate and its optical isomers.

Generally, two optically pure compounds which are in mirror image relationship to one another possess the same physical properties, except one-optical activity. In detail, the two enantiomers are completely or almost identical in, for example, melting point, boiling point, solubility, density and refractive index, but completely opposite in optical rotation. Since the two enantiomers rotate the plane of polarized light in equal but opposite directions, no net optical rotation is observed when they are mixed. In other words, the optical rotation of a racemate is zero in theory and near zero in practicality.

The difference in optical rotation, that is, in the spatial arrangement of four groups connected to the chiral atom, i.e., configuration, frequently causes a significant distinction between one enantiomer and its racemate in physiological activity and toxicity. However, since there is no consistent relationship between configurational difference and its influences, it is actually impossible to deduce them from the prior arts. For instance, levofloxacin, a (−) optical isomer, is known to show two-fold higher antibacterial activity than ofloxacin, a racemate, and 8–128 fold higher than the other enantiomer, (+)-ofloxacin (*Drugs of the future*, 17(7): 559–563 (1992)). An example of a relation between configuration and toxicity may be referred to cisapride (Stephen C. Stinson, *Chemical & Engineering News*, 76(3), 3 (1998)). Stephen C. Stinson revealed that the racemate (±)-cisapride, when used in combination with other drugs, may, cause a toxic effect whereas (+)-norcisapride does not, concluding that (−)-cisapride is causative of the toxicity of the racemate. Korean Pat. No. 179,65 describes 1-(5-hydroxyhexyl)-3-methyl-7-propylxanthine, showing that its R-(−) isomer is at least three-fold more potent in cerebral blood flow-stimulating action and three-fold longer in the duration time of activity than the S-(+) isomer. However, in the case of temafloxacin, its racemate and its enantiomers show no differences in antibacterial activity and pharmacokinetics (Daniel T. W. Chu, et al., *J. Med. Chem.*, 34, 168–174 (1991)).

As aforementioned, due to unexpected physiological differences, between a racemate and its optically pure enantiomers (i.e. activity, P.K., toxicity, etc.), a racemate must be resolved into its corresponding enantiomers. As can be recognized from the above, the use of a racemate, as it is, can be problematic though its one enantiomer shows excellent pharmacological effects and no toxicity, if the other enantiomer has any toxicity. This phenomenon can be frequently found in many pharmacologically effective compounds. In addition, when a pharmacologically effective racemate is used as it is, the two enantiomers are administered at the same dose. Which If one enantiomer is pharmacologically inactive, only results in imposing a load, on the body. Therefore, it is very important to resolve a racemate into pure compounds for better pharmacological effects and lower toxicity.

On the basis of aforementioned prior arts, through the intensive and thorough research on quinolone antibacterial agents, repeated by the present inventors found that 4-aminomethyl-4-methyl-3-(Z)-alkoxyimino pyrrolidine derivatives causing optical activity, when being attached to 7-positions of quinclone nuclei, endows optically active quinoline carboxylic acid derivatives with highly potent antibacterial activity and excellent pharmacokinetic properties.

Hence, the optically active quinoline carboxylic acid derivatives according to the present invention show greatly improved antibacterial activity against Gram-positive bacteria, especially against methicilline-resistant staphylococci and increasing quinolone-resistant strains, compared with their racemates, their counterpart enantiomers and the using quinolones. Also, according to the present invention the compounds are excellent in pharmacokinetic profiles and hardly cause phototoxicity in spite of bearing halogen atoms at 8-position.

DISCLOSURE OF INVENTION

The present invention provides optically active quinoline carboxylic acid derivatives with 4-aminomethyl-4-methyl-3-(Z)-alkoxyiminopyrrolidine substitutents at the 7-position of the quinolone nuclei, represented by the following formula 1, their pharmaceutically acceptable salts, and their solvates:

Formula 1

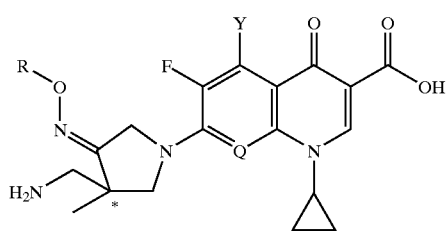

wherein, Q is C—H, C—F, C—Cl or N; Y is H or NH$_2$; R is a straight or branched alkyl group of C$_1$–C$_4$, an allyl group, or a benzyl group; and * represents an optically pure chiral carbon atom.

The optically active quinoline carboxylic acid derivatives of the formula 1 possess highly potent antibacterial activity against a wide range of bacteria, especially quinolone-resistant bacteria, and show excellent pharmacokinetic behaviors with markedly reduced toxicity. The substituent at the 7-position of the quinolone carboxylic acid derivative contains a chiral carbon atom at its 4-position of the pyrrolidine moiety and thus makes the substituent-bearing quinolones optically active.

In adddtion, the present invention provides a process for the preparation of optically active quinoline carboxylic acid.

Also, the present invention provides optically active ketal derivatives represented by formula 2 which is a starting material useful for preparing the optically pure quinoline carboxylic acid derivatives.

Formula 2

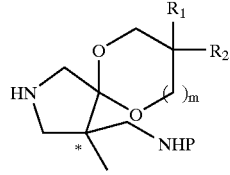

Wherein R$_1$ and R$_2$ are H or methyl, R$_1$ and R$_2$ are the same; P is H or an amine-protecting group; m is 0 or 1; and * represents an optically pure chiral carbon atom.

Hereinafter, the present invention is described in detail.

Of the compounds represented by the formula 1, preferable compounds are those wherein R is an alkyl group of C$_1$–C$_2$ or an alkyl group; Q represents C—H, C—F or N; Y is H or NH$_2$. These compounds are far superior to ciprofloxacin and sparfloxacin, representatives of conventional quinolone antibacterial agents in activity, pharmacokinetics, and toxicities. Compared with the racemates and the other enantiomers, the optically pure compounds of the present invention showed potent antibacterial activity especially against Gram-positive bacteria and quinolone-resistant strains, and was found out to be safe.

By virtue of the potent antibacterial activity against Gram-positive bacteria as well as Gram-negative bacteria and of excellent pharmacokinetic profiles, therefore, the optically active compounds of thie present invention can treat even at smaller doses diseases that preexisting antibiotics and quinolone antibacterial agents have not yet been able to control. Also, compared with their corresponding racemates and enantiomers, as mentioned above, the compounds of the present invention are greatly improved in the antibacterial activity especially against Gram-positive bacteria and quinolone-resistant strains, so that their effective dosage can be significantly reduced to at least half of the conventional ones. In conclusion, the optically active compounds of the present invention are expected to impose a lighter physiological burden on the body while showing more improved in vivo efficacy.

It is known that serious phototoxicity occurs as a side effect when a halogen atom is introduced into the 8-position of the quinolone nucleus. In the compound of the present invention, a halogen atom is substituted at the 8-position, as well. When being exposed for 48 hours to a UVA light source, mice which had been administered with a racemate beating a halogen atom, at 8-position showed moderate, edema and erythema as their ears were measured to be thicker by 39% than before the exposure. On the other hand, in the case of the mirror image ones of the compounds of the present invention and sparfloxacin, mice experienced serious edema and erythema as their ears became thicker by 150% under the same exposure condition than before the exposure. In contrast, the optically active compound of the present invention was found out to hardly cause edema and erythema. Hence, even when containing a halogen atom at the 8-position nuclei, the compound of the present invention is almost free of phototoxicity, so that it can be used as an effective antibacterial agent with greatly reduced side effects.

Over other enantiomers of compounds of the present invention, corresponding racemates, and conventional antibacterial agents, the optically active quinoline carboxylic acid derivatives according to the present invention represented by the formula 1 have advantage of being superior in antibacterial activity, and in vivo pharmacokinetic properties and being free of phototoxicity. Therefore, they can exert excellent antibacterial activity even at small doses. In addition, the optically active quinoline carboxylic acid derivatives of the present invention, represented by the formula 1, are endowed with greatly improved antibacterial activity against Gram-positive bacteria and exert sufficient antibacterial activity especially against methicillin-resistant staphylococci and increasing quinolone-resistant strains.

For use, the compounds of the formula 1 may be produced as pharmaceutically acceptable salts. Preferable are acid-addition salts which are formed by pharmaceutically acceptable free acids. For the free acids, inorganic or organic acids can be used. Available inorganic acids are exemplified by hydrochloric acid, phosphoric acid, and sulfuric acid, Examples of the organic acids include methane sulfonic acid, p-toluenesulfonic acid, acetic acid, citric acid, maleic acid, succinic acid, oxalic acid, benzoic acid, tartaric acid, fumaric acid, mandelic acid (phenylglycolic acid), lactic acid, glycolic acid, gluconic acid, galacturonic acid, glutamic acid, and aspartic acid. The compound of the formula 1 may also be used in pharmaceutically acceptable metal salts. Such salts include salts with sodium and potassium. Pharmaceutically acceptable salts of the optically active quinoline carboxylic acid derivatives according to the present invention can be prepared according to a conventional conversion method.

Also, the present invention provides a method for preparing optically active quinoline carboxylic acid derivatives of the formula 1.

The optically active quinoline carboxylic acid derivative of the formula 1 is prepared as indicated in the following reaction scheme 1:

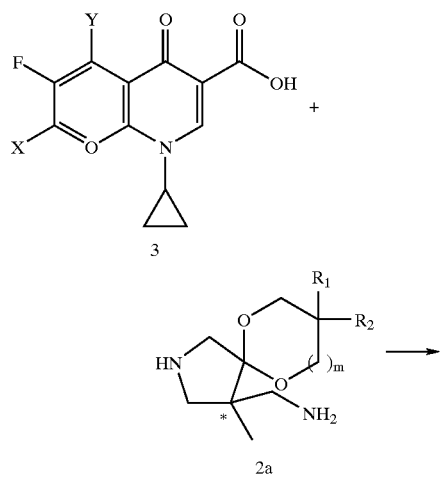

Scheme 1

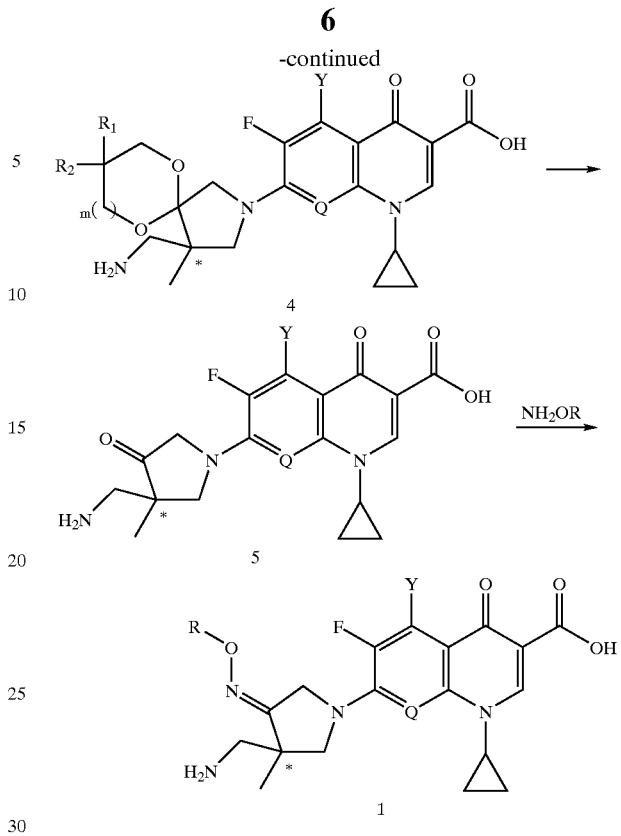

wherein, Q, Y, R, $R_1$, $R_2$, m and * are each as defined above; X is a halogen atom, preferably a fluorine or a chlorine atom.

As depicted in the reaction scheme 1, a method for preparing an optically active quinoline carboxylic acid derivative of the formula 1 comprises the following steps:

1) condensing the compound of formula 3 with the ketal compound of formula 2a, in the presence of an acid acceptor to give an optically active quinoline carboxylic acid derivative, represented by formula 4;
2) deketalizing the compound of formula 4 to give a pyrrolidinone compound of formula 5; and
3) reacting the pyrrrolidinone compound of formula 5 with an alkoxylamine in the presence of a base to obtain the desired compound of formula 1.

The compound of the formula 3, used as a starting material for this reaction scheme, can be prepared according to the method disclosed in U.S. Pat. No. 4,382,892. The compound of formula 2a may be used in a free base or acid salt, which can be formed by, an acid, such as hydrochloric acid, acetic acid, and trifluoroacetic acid.

In the condensation step (the step 1 in the above reaction scheme 1), the compound of formula 3 as the starting material is reacted with the optically active pyrrolidine derivative of formula 2a for 1–24 hours in a solvent in the presence of an appropriate base (acid acceptor) to afford the optically active quinoline carboxylic acid of formula 4. Thus, the subsequent compounds, represented by the formula 5 and 1, all are to be of optical activity. As for the reaction temperature of the condensation, it is within the range of 0–150° C. and preferably within the range of room temperature to 90 ° C. The condensation occurs in an organic solvent, preferable examples of which include alcohols such as methanol, ethanol and isopropyl alcohol, acetonitrile, N,N-dimethylformamide (DMF), dimethylsulfoxide (DMSO), and pyridine. Available bases (acid acceptor) are inorganic bases, such as sodium hydrogen carbonate, potassium carbonate, sodium carbonate, and organic bases, such as triethylamine, diisopropylethylamine, pyridine, lutidine, N,N-dimethylaniline, N,N-dimethylaminopyridine, 1,8-diazabicyclo[5.4.0]undec-7-ene (DBU), 1,5-diazabicyclo[4.3.0]nonene-5 (DBN), and 1,4-diazabicyclo[2.2.2]octane (DABCO). When used at excess amounts (e.g., 2–5 mole equivalents), the compound of formula 2a serves as an acid acceptor as well as a reactant so as to enhance the reaction efficiency.

In the deketalization step (the step 2 in the reaction scheme 1), the ketal compound of formula 4 is converted into the pyrrolidinone compound of formula 5 with the aid of an acid. This dekatalization step is preferably conducted at room temperature to 100° C. The acid available in this deketalization may be exemplified by hydrochloric acid, hydrobromic acid, sulfuric acid, acetic acid, methane sulfonic acid, and trifluoromethane sulfonic acid.

In the step 3 in the reaction scheme 1, the pyrrolidinone compound of formula 5 is reacted with an alkoxylamine at 0–90° C. in the presence of an appropriate base to produce the optically active quinoline carboxylic derivative of the formula 1. In this regard, pyridine can be used as not only a solvent, but also a base. Where water, tetrahydrofuran or alcohol (methanol, ethanol) is employed as a solvent, an inorganic base, such as sodium hydrogen carbonate or sodium acetate is useful as a base.

Optically active quinoline carboxylic acid derivatives of the formula 1 are also prepared as indicated in the following reaction scheme 2:

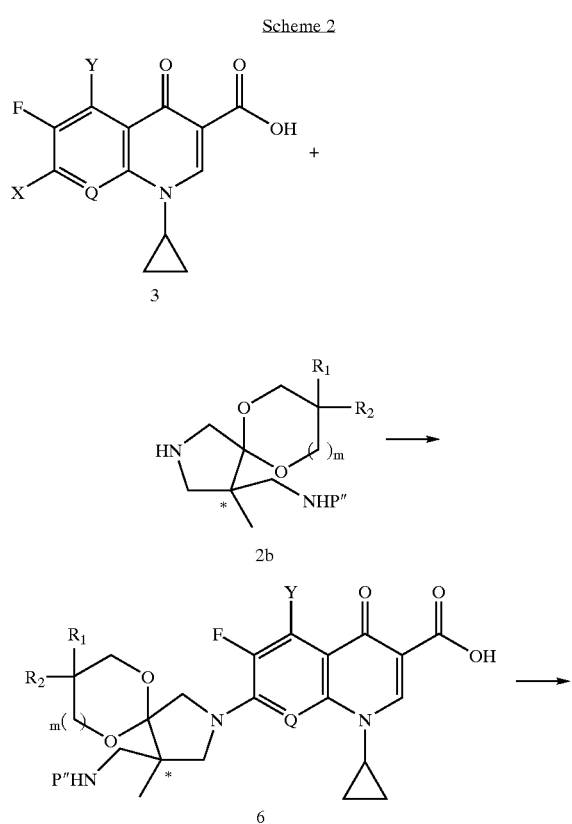

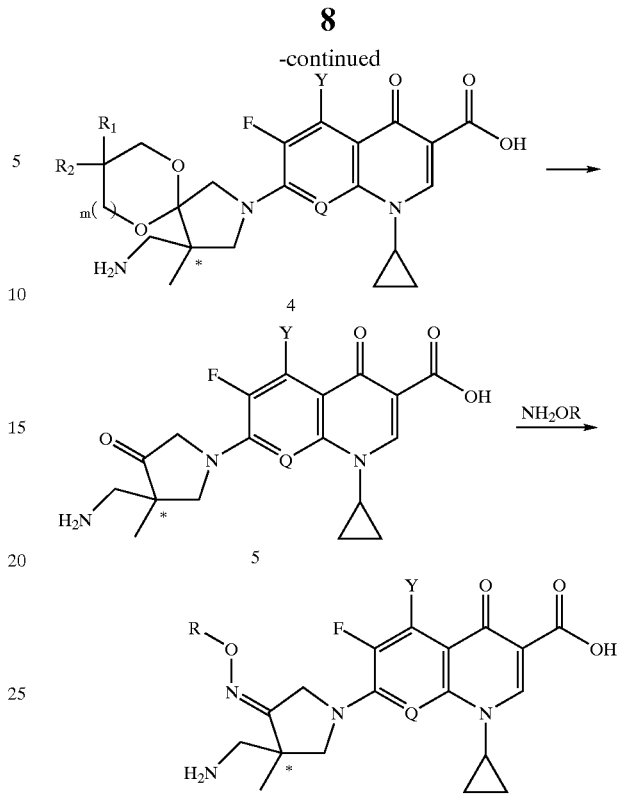

wherein, Q, X, Y, R, $R_1$, $R_2$, m and * are each as defined above, and P" is an amine-protecting group. Examples of the amine-protecting group include formyl, acetyl, trifluoroacetyl, benzoyl, alkoxycarbonyl (e.g., methoxycarbonyl, ethoxycarbonyl, t-butoxycarbonyl, benzyloxycarbonyl, p-methoxybenzyloxycarbonyl, and trichloroethoxycarbonyl), benzyl, p-methoxybenzyl, and trityl.

As depicted in the reaction scheme 2, another method for preparing an optically active quinoline carboxylic acid derivative of the formula 1 comprises the following steps:

1) condensing the compound of formula 3, with the ketal compound of formula 2b having a protected amine group, in the presence of an acid acceptor to give an intermediate of formula 6;

2) deprotecting the amine-protecting group (p") from the intermediate of formula 6, through the suitable deprotecting method to give a compound of formula 4;

3) deketalizing the compound of formula 4 to give a pyrrolidinone compound of formula 5; and 4) reacting the pyrrolidinone compound of formula 5 with an alkoxylamine to obtain the desired compound of formula 1.

In the condensation step(the step 1 of the above reaction scheme 2), the same reaction condition as in the condensation step of the reaction scheme 1 applied to produce the ketal compound of formula 6 from the compound of formula 3 and the compound of formula 2b.

In the deprotecting step (the step 2 of the reaction scheme 2), the amine-protecting group P" of the ketal compound of formula 6 is removed by an appropriate method, for example, acid or alkali hydrolysis or another deprotecting process, to afford the compound of formula 4 in which the amine group is bared.

The deprotection of the amine group may be accomplished by reacting the compound of formula 6 in the presence of an acid or a base at room temperature to 120° C. in a solvent. Available for the deprotection are inorganic acids, such as hydrochloric acid, hydrobromic acid, and sulfuric acid, and organic acids, such as acetic acid, trifluoroacetic acid, formic acid, and p-toluenesulfonic acid. The alkali hydrolysis of the protecting group P″ may be achieved by use of a base such as sodium hydroxide, sodium carbonate, potassium carbonate, sodium methoxide, sodium ethoxide, and sodium acetate. In the case that the protecting group P″ is benzyl, p-methoxybenzyl, benzyloxycarbonyl, p-methoxybenzyloxycarbonyl, or trichloroethoxycarbonyl, its removal can be fulfilled by conducting a catalytic reduction reaction at 5–100° C. under a hydrogen atmosphere in the presence of a catalyst, such as palladium, Raney-nickel, and platinum.

Use of an acid can remove not only the protecting group P″, but also the ketal group from the ketal compound of formula 6. Suitable for both the deprotection and deketalization of the ketal compound is hydrochloric acid, hydrobromic acid, sulfuric acid, trifluoroacetic acid or methanesulfonic acid.

The step 3 and the step 4 in which the desired compound of the formula 1 is prepared from the compound of formula 4 via the pyrrolidinone compound of formula 5 are respectively carried out under the same conditions as in the respective corresponding steps of the reaction scheme 1.

The present invention also provides an optically active ketal derivative, represented by the formula 2, which is a starting material for the optically active quinoline carboxylic acid derivative of the formula 1. The optically active ketal derivative of interest is represented by formula 2a or 2b.

The ketal derivatives of the present invention are prepared as indicated in the following reaction scheme 3.

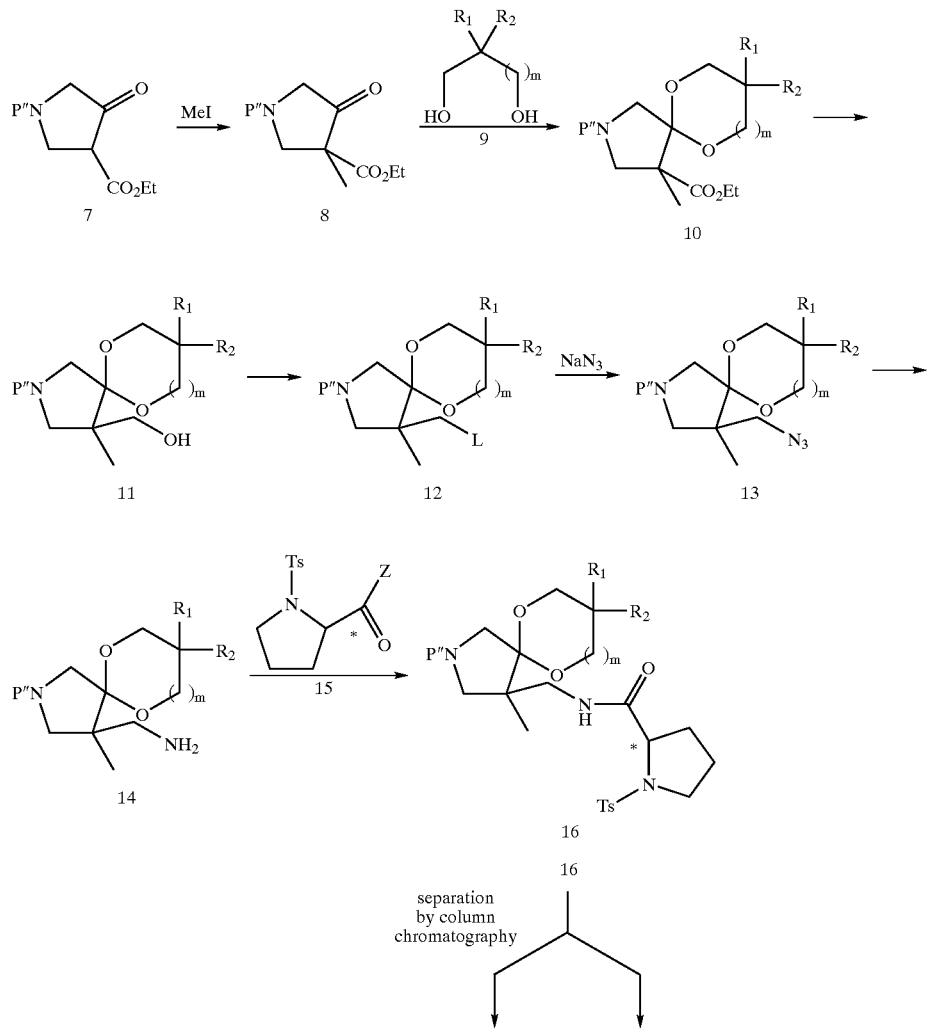

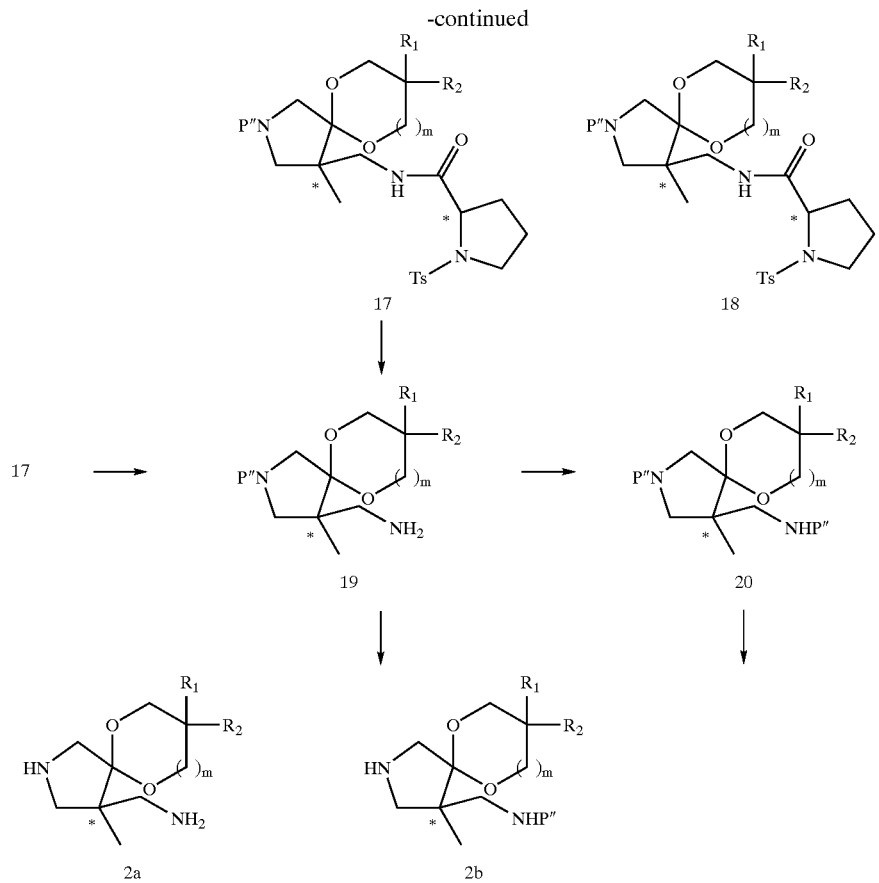

wherein, $R_1$, $R_2$, m and * are each as defined above; L is methanesulfonyloxy or paratoluenesulfonyloxy; Z represents a chlorine atom or $O—CO—R_3$ wherein $R_3$ is ethyl, isopropyl or isobutyl; P' and P", which may be the same or different, are an amine protecting group.

As indicated in the reaction scheme 3, the optically active ketal derivative, represented by formula, 2, can be prepared by a method comprising the steps of:

1) reacting the compound of formula 7 with iodomethane in the presence of an appropriate base to give the compound of formula 8, which has a methyl group attached to its pyrrolidine ring (step 1);
2) reacting the compound of formula 8 with the compound of formula 9 in the presence of an acid catalyst to give the ketal compound of formula 10 (step 2);
3) reducing the ester group in the ketal compound of formula 10 to give the hydroxy methyl compound of formula 11 (step 3);
4) transforming the hydroxy group (—OH) of the compound of formula 11 into an appropriate leaving group L to give the compound of formula 12 (step 4);
5) reacting the leaving group L of the compound of formula 12 with sodium azide to give the azidomethyl pyrrolidine compound of formula 13 (step 5);
6) reducing the compound of formula 13 to give the compound of formula 14 (step 6);
7) reacting the compound of formula 14 with the proline derivative of formula 15 to give the diastereomer mixture of formula 16 (step 7);
8) separating the diastereomer mixture of formula 16 into each diastereomer of formula 17 and 18 (step 8);
9) removing the prolyl group of the desired diastereomer of formula 17 to give the optically pure compound of formula 19 (step 9); and
10) removing the amine-protecting group P' from the compound of formula 19 to give the desired compound of formula 2a, or introducing an amine-protecting group P" into the compound of formula 19 to give the compound of formula 20, followed by removing the amine-protecting group P' to obtain the desired compound of formula 2b. (step 10).

In the step 1, the beta-ketoester compound of formula 7 is reacted with iodomethane ($CH_3I$) at 30–70° C. in the presence of an appropriate base to introduce a methyl group into the pyrrolidine ring as illustrated by formula 8. Suitable for use as the base is sodium hydrogen carbonate, sodium carbonate or potassium carbonate.

In the step 2, the compound of formula 8 is reacted with the glycol compound of formula 9 in the presence of an acid catalyst such as paratoluene sulfonic acid, to give the ketal compound of formula 10.

In the step 3, using lithium aluminum hydride or sodium borohydride, the ester group of the ketal compound of formula 10 is reduced to give the hydroxymethyl compound of formula 11. In cooperation with a lithium salt such as lithium chloride or lithium bromide, sodium borohydride can further enhance the reaction rate.

In the step 4, the hydroxy group (—OH) of the compound of formula 11 is transformed into an appropriate leaving group L such as methanesulfonyloxy (—OMs) or paratoluenesulfonyloxy (—OTs). In this regard, the compound of formula 11 is reacted with methane sulfonylchloride or paratoluenesulfonyl chloride at 0–50° C. in the presence of an organic base such as triethylamine or pyridine.

In the step 5, the leaving group L of the compound of formula 12 is allowed to react with sodium azide to give an azidomethyl pyrrolidine compound of formula 13. Suitable for use as a solvent for this reaction is N,N-dimethylformamide (DMF) or dimethyl sulfoxide (DMSO).

In the step 6, a metal catalyst such as platinum, palladium on carbon (Pd/C), or Raney-nickel is used to reduce the azido group of the compound of formula 13. Alternatively, the reduction of the azido group is carried out in the presence of triphenylphosphine or triphenylphosphite in an inert solvent such as tetrahydrofuran. In result, an aminomethyl pyrrolidine compound of formula 14 is obtained in good yield.

In the step 7, condensation is induced to form an amide bond between the compound of formula 14 and the optically pure proline derivative of formula 15. The proline derivative can be used in a form of N-tosyl-L-prolyl chloride or N-tosyl-L-proline. Where the compound of formula 14 is reacted with N-tosyl-L-prolyl chloride, the condensation is carried out in the presence of a base. For use in this condensation, an organic base, such as triethyl amine, 1,8-diazabicyclo[5.4.0]-undec-7-ene (DBU) or 1,5-diazabicyclo[4.3.0]non-5-ene (DBN), or an inorganic base, such as sodium carbonate or sodium hydrogen carbonate, is available. Dichloromethane, chloroform, acetonitrile, or dimethylformamide can be used as a solvent. This reaction is preferably conducted at −25–30° C. In the case of the condensation of the compound of formula 14 with N-tosyl-L-proline, N-tosyl-L-proline is activated into a mixed anhydride by use of alkylchloroformate such as ethylchloroformate and then, reacted with the compound of formula 14. The reaction conditions are the same as set forth in the case of N-tosyl-L-prolyl chloride.

In the step 8, the compound of formula 16, which is a diastereomer mixture, is separated by column chromatography into each diastereomer which are represented by the structural formula 17 and 18.

In the step 9, the desired diastereomer of formula 17 is hydrolyzed by use of a base such as sodium hydroxide and potassium hydroxide to obtain the optically pure compound of formula 19, which is deprived of the prolyl group.

In the step 10, the compound, of formula 2a is obtained by deprotecting the amine-protecting group P' from the compound of formula 19. In the case of the compound of formula 2b, the deprotection is preceded by the introduction of the amine-protecting group P'' to the compound of formula 19. That is, the compound of formula 19 is introduced with the amine-protecting group P'' to give the compound of formula 20, from which the amine-protecting group P' is removed. The deprotection process is carried out under the same conditions as in the deprotection of the amine-protecting group P'' from the compound of formula 6 to give the compound of formula 4 in the reaction scheme 2.

REST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention .

Preparation Example 1

Preparation of 1-benzyloxycarbonyl-4-ethoxycarbonyl-4-methylpyrrolidin-3-one

To the solution of N-benzyloxycarbonyl-4-ethoxycarbonylpyrrolidin-3-one (291 g) in acetone (1.5 l) was added potassium carbonate (200 g), followed by iodomethane (300 mL), and then the solution was refluxed for 3 hr. The reaction mixture was cooled at room temperature, filtered, and concentrated under reduced pressure. The residue was purified by silica gel column chromatography (ethyl acetate:n-hexane=1:6) to obtain the desired compound, (237.7 g, 80.7%).

$^1$H-NMR(CDCl$_3$, ppm) 1.16(3H, t, J=7.1 Hz), 1.36(3H, s), 3.49(1H, d, J=12.0 Hz), 3.83(1H, d, J=19.3 Hz), 4.00–4.17(3H, m), 4.35(1H, d, J=11.7 Hz), 5.16(2H, s), 7.19–7.33(5H, m).

Preparation Example 2

Preparation of 2-benzyl 4-ethyl 4,8,8-trimethyl-6,10-dioxa-2-azaspiro[4.5]decane-2,4-dicarboxylate To the solution of the compound (214 g) obtained from the above preparation example 1 in n-heptane (1 l) was added neopentylglycol (219 g), followed by paratoluenesulfonic acid (35 g), and then the solution was refluxed for 6 hr. The reaction mixture was concentrated under reduced pressure. The residue was diluted in CH$_2$Cl$_2$ (1 l), and washed with saturated NaHCO$_3$ solution and water. The organic layer was dried over anhydrous magnesium sulfate, concentrated under reduced pressure, and the residue was purified by silica gel column chromatography (ethyl acatate:n-hexane=1:6) to obtain the desired compound (235 g, 85.7%).

$^1$H-NMR(CDCl$_3$, ppm) 0.72(3H, s), 1.19(3H, s), 1.25~1.28(3H, m), 1.34(3H, s), 3.34–3.60(6H, m), 3.96(1H, d, J=10.8 Hz), 4.08(1H, d, J=11.4 Hz), 4.11–4.16(1H, m), 4.23–4.25(1H, m), 5.14(2H, d, J=4.6 Hz), 7.30–7.38(5H, m)

Preparation Example 3

Preparation of ethyl 4,8,8-trimethyl-6,10-dioxa-2-azaspiro[4.5]decane-4-carboxylate To the solution of the compound (230 g) obtained from the preparation example 2 in methanol (2 l) was added 10% Pd-C 11.5 g, and the solution was stirred for 1.5 hr under hydrogen atmosphere. The reaction mixture was filtered and concentrated under reduced pressure to obtain the desired compound (131 g, 86.8%).

$^1$H-NMR(CDCl$_3$, ppm) 0.30(3H, s), 0.75(3H, s), 0.82–0.86(6H, m), 2.10(1H, s), 2.26(1H, d, J=12.0 Hz), 2.44(1H, d, J=12.2 Hz), 2.97–3.11(4H, m), 3.26(1H, d, J=11.7 Hz), 3.70–3.79(2H, m)

Preparation Example 4

Preparation of ethyl 2-benzyl-4,8,8-trimethyl-6,10-dioxa-2-azaspiro[4.5]decane-4-carboxylate To the solution of the compound (128.3 g) obtained by the preparation example 3 in acetonitrile (1 l) was added potassium carbonate (103 g) followed by benzylchloride (69 ml), and the solution was refluxed for 16 hr. The reaction mixture was cooled at room temperature, filtered and concentrated under reduced pressure. The residue was purified by silica gel column chromatography (CH$_2$Cl$_2$ 100%) to obtain the desired compound (204.2 g, 93.1%).

$^1$H-NMR(CDCl$_3$, ppm) 0.66(3H, s), 1.16(3H, s), 1.22–1.28(3H, m), 1.39(3H, s), 2.65(1H, d, J=9.0 Hz), 2.83(1H, d, J=10.0 Hz), 3.10(1H, d, J=9.8 Hz), 3.19(1H, d, J=9.3 Hz), 3.34–3.39(2H, m), 3.45–3.51(2H, m), 3.61(1H, d, J=13.4 Hz), 3.74(1H, d, J=13.2 Hz), 4.12–4.20(2H, m), 1.21–7.35(5H, m)

Preparation Example 5

Preparation of 2-benzyl-4-hydroxymethyl-4,8,8-trimethyl-6,10-dioxa-2-azaspiro[4.5]decane

To the solution of the compound (188 g) obtained by the preparation example 4 in THF (2 l) was added LiAlH$_4$ (30.8 g) at 0~5° C. for 30 min, and the reaction mixture was stirred for 30 min. Water (400 ml) and 10% NaOH solution (200 ml) was added to the reaction mixture slowly with keeping between 0~5° C., and the generated solid was filtered. Then the filterate was evaporated. The remaining solution was extrated with diethylether, and ether layer was dried over anhydrous magnesium sulfate and concentrated under reduced pressure to obtain the desired compound (152.9 g, 92.5%).

$^1$H-NMR(CDCl$_3$, ppm) 0.18(3H, s), 0.52(3H, s), 0.66(3H, s), 1.97(1H, d, J=79.0 Hz), 2.30(2H, d, J=9.8 Hz), 2.60(1H, d, J=10.0 Hz), 2.90–2.97(4H, m), 3.11–3.16(4H, m), 6.71–6.80(5H, m)

Preparation Example 6

Preparation of 2-benzyl-4-methanesulfonyloxymethyl-4,8,8-trimethyl-6,10-dioxa-2-azaspiro[4.5]decane

To the solution of the compound (145.1 g) obtained by the preparation example 5 in CH$_2$Cl$_2$ (1.5 l) was added triethylamine (79.5 ml), followed by methanesulfonylchloride (36.8 ml) at 0~5° C. The reaction temperature was warmed up to room temperature slowly, and then the solution was stirred for 2 hr. The reaction mixture was washed with water and saturated NaCl solution, dried over anhydrous magnesium sulfate, filtered, and concentrated under reduced pressure to obtain the desired compound (177.1 g, 97.2%).

$^1$H-NMR(CDCl$_3$, ppm) 0.62(3H, s), 1.08(3H, s), 1.09(3H, s), 2.33(1H, d, J=9.0 Hz), 2.70–2.77(2H, m), 2.84(3H, s), 3.07(1H, d, J=10.2 Hz), 3.27(2H, s), 3.32(2H, s), 4.10(1H, d, J=9.5 Hz), 4.35(1H, d, J=9.3 Hz), 7.17–7.26(5H, m)

Preparation Example 7

Preparation of 2-benzyl-4-azidomethyl-4,8,8-trimethyl-6,10-dioxa-2-azaspiro[4.5]decane

To the solution of the compound (160 g) obtained by the preparation example 6 in DMF (1 l) was added NaN$_3$ (68 g), and the solution was stirred at 110~120° C. for 6 hr. The reaction mixture was concentrated under reduced pressure, diluted with diethyl ether (1 l) and washed with water. Ether layer was dried over anhydrous magnesium sulfate, filtered, and concentrated under reduced pressure. The remaining solution was purified by silica gel column chromatography ethyl acetate:n-hexane=1:20) to obtain the desired compound (127 g, 83.1%).

$^1$H-NMR (CDCl$_3$, ppm) 0.17(3H, s), 0.60(3H, s), 0.65 (3H, s), 1.92(1H, d, J=9.0 Hz), 2.24(1H, d, J=9.0 Hz), 2.34(1H, d, J=10.0 Hz), 2.53(1H, d, J=10.2 Hz), 2.87–2.95 (5H, m), 3.03(1H, d, J=12.0 Hz), 3.10–3.19(2H, m), 6.72–6.82(5H, m)

Preparation Example 8

Preparation of (−)-2-benzyl-4-(N-tosyl-L-prolyl) aminomethyl-4,8,8-trimethyl-6,10-dioxa-2-azaspiro [4.5]decane

To the solution of the compound (125 g) obtained by preparation example 7 in ethylacetate (1 l) was added 50% Raney-Nickel slurry (72 ml), and the solution was stirred for 3 hr under hydrogen atmosphere. The reaction mixture was filtered, and concentrated under reduced pressure to obtain 2-benzyl-4-aminomethyl-4,8,8-trimethyl-6,10-dioxa-2-azaspiro[4.5]decane (107.5 g). The compound was used for the further reaction without purification.

To the solution of N-tosyl-L-proline (104.6 g) in CH$_2$Cl$_2$ (15 l) was added triethylamine (123 ml), followed by ethylchloroformate (38 ml) slowly at 0~5° C. for 30 min. At the same temperature, 2-benzyl-4-aminomethyl-4,8,8-trimethyl-6,10-dioxa-2-azaspiro[4.5]decane (107.5 g) obtained previously was added to the reaction mixture. The mixture was warmed up slowly and stirred at room temperature for 2 hr. The reaction mixture was washed with water (1 l), dried over anhydrous magnesium sulfate, filtered, and concentrated under reduced pressure. The residue was purified by silica gel column chromatography (ethyl acetate:n-hexane=2:3) to give the desired compound (68.7 g, 32.7%).

$^1$H-NMR(CDCl$_3$, ppm) 0.72(3H, s), 1.05(3H, s), 1.26(3H, s), 1.451~1.55(1H, m), 1.60~1.65(1H, m), 1.70~1.75(1H, m), 2.20~2.25(1H, m), 2.44(3H, s8, 2.52(1H, d, J=8.8 Hz), 2.67(1H, d, J=8.8 Hz), 2.89(1H, d, J=10.2 Hz), 3.11~3.15 (2H, m), 3.43~3.60(6H, m), 3.65~3.67(3H, m), 4.08~4.11 (1H, m), 7.23~7.35(6H, m), 7.71(2H, d, J=8.3 Hz), 7.87~7.90(1H, m)

$[\alpha]_D$=−167.86(c=0.32, CHCl$_3$, 25.0° C.)

Preparation Example 9

Preparation of (+)-2-benzyl-4-(N-t-butoxycarbonyl) aminomethyl-4,8,8-trimethyl-6,10-dioxa-2-azaspiro [4.5]decane

The compound obtained from the preparation example 8 (17.5 g) and KOH (30 g) were dissolved in isopropyl alcohol (250 ml) and the solution was stirred and refluxed for 7 hr. After the reaction was over, the solvent was evaporated. The remaining solution was diluted with water (250 ml) and extracted with diethylether twice. The combined ether was dried over anhydrous magnesium sulfate, filtered, and concentrated under reduced pressure to obtain (+)-2-benzyl-4-aminomethyl-4,8,8-trimethyl-6,10-dioxa-2-azaspiro[4.5] decane (9.5 g). The compound was used for the further reaction without purification.

(+)-2-benzyl-4-aminomethyl-4,8,8-trimethyl-6,10-dioxa-2-azaspiro[4.5]decane (9.5 g) obtained previously and di-t-butyl dicarbonate (8.2 g) were dissolved in CH$_2$Cl$_2$ (150 ml) and the reaction mixture was stirred at room temperature for 30 min. The reaction mixture was concentrated under reduced pressure and the residue was purified by silica gel column chromatography (ethyl acetate:n-hexane=1:3) to obtain the desired compound (12.4 g, 97.2%).

$^1$H-NMR(CDCl$_3$, ppm) 0.60(3H, s), 0.93(3H, s), 1.09(3H, s), 1.36(9H, s), 2.36(1H, d, J=9.0 Hz), 2.58(1H, d, J=9.0 Hz), 2.71(1H, d, J=10.3 Hz), 2.94(1H, d, J=10.3 Hz), 3.17(2H, d, J=7.6 Hz), 3.33(2H, s), 3.40(2H, s), 3.54(2H, s), 5.33(1H, bs), 7.14~7.24(5H, m)

$[\alpha]_D$=+0.65(c=5.07, CHCl$_3$, 25.0° C.)

Preparation Example 10

Preparation of (+)-4-(-t-butoxycarbonyl) aminomethyl-4,8,8-trimethyl-6,10-dioxa-2-azaspiro [4.5]decane

To the solution of the compound obtained from the preparation example 9 (12.4 g) in MeOH (150 ml) was added 10% Pd-C (7.0 g), and the solution was stirred for 2 hr under hydrogen atmosphere. The reaction mixture was filtered and concentrated under reduced pressure to obtain the desired compound (8.1 g, 84.0%).

$^1$H-NMR(CDCl$_3$, ppm) 0.70(3H, s), 1.00(3H, s), 1.15(3H, s), 1.40(9H, s), 2.46(1H, bs), 2.67(1H, d, J=11.0 Hz), 2.89(1H, d, J=12.0 Hz), 3.04(1H, d, J=12.0 Hz) 3.15~3.28 (3H, m), 3.43~3.52(3H, m), 5.12(1H, bs)

$[\alpha]_D$=+129.54(c=0.48, CHCl$_3$, 25.0° C.)

EXAMPLE 1

Preparation of (+)-7-(4-{[(N-t-butoxycarbonyl) amino]methyl}-4,9,8-trimethyl-6,10-dioxa-2-azaspiro[4.5]dec-2-yl)-1-cyclopropyl-6-fluoro-4-oxo-1,4-dihydro[1,8]naphthyridine-3-carboxylic acid The compound obtained from the preparation example 10 (4.44 g), 1-cyclopropyl-6-fluoro-7-chloro-4-oxo-1,4-dihydro[1,8] naphthyridine-3-carboxylic acid (3.45 g), and triethylamine (2.6 ml) were added to acetonitrile (50 ml) in order and the reaction mixture was stirred at 45~5° C. for 4 hr. The precipitate was filtered and dried to obtain the desired compound (5.31 g, 77.6%).

$^1$H-NMR (CDCl$_3$, ppm) 0.80(3H, s), 1.07(2H, bs), 1.17 (3H, s), 1.24(5H, bs), 1.26(2H, bs), 1.41(9H, s), 3.40(2H, bs), 3.55~3.60(5H, m), 4.05~4.32(4H, m), 5.07(1H, bs), 8.03(1H, d, J=12.4 Hz), 8.71(1H, s)

$[\alpha]_D$=+9.77(c=1.19, CHCl$_3$, 25.0° C.)

EXAMPLE 2

Preparation of (+)-5-amino-7-(4-{[(N-t-butoxycarbonyl)amino]methyl}-4,8,8-trimethyl-6,10-dioxa-2-azaspiro[4.5]dec-2-yl)-1-cyclopropyl-6,8-difluoro-4-oxo-1,4-dihydro-3-quinolinecarboxylic acid The compound (5.5 g) obtained from the preparation example 10 and 5-amino-1-cyclopropyl-6,7,8-trifluoro-4-oxo-4-dihydro-3-quinolinecarboxylic acid (2.48 g) were dissolved in acetonitrile (24 ml), and refluxed for 6 hr. The reaction mixture was concentrated under reduced pressure, and the residue was purified by silica gel column chromatography (CHCl$_3$:MeOH=9:1) to obtain the desired compound (3.5 g, 70%).

$^1$H-NMR(CDCl$_3$, ppm) 0.74(3H, s), 1.03(2H, bs), 1.15 (5H, bs), 1.25(3H, s), 1.41(9H, s), 3.30~3.37(2H, m), 3.39~3.57(5H, m), 3.74(1H, d, J=9.5 Hz), 3.84(1H, m), 3.95(1H, d, J=11.0 Hz), 4.03(1H, d, J=10.7 Hz), 5.14(1H, bs), 6.36(1H, bs), 8.51(1H, s)

$[\alpha]_D$=+175.42(c=0.52, CHCl$_3$, 25.0° C.)

EXAMPLE 3

Preparation of (−)-7-(4-{[N-t-butoxycarbonyl) amino]methyl}-4,8,8-trimethyl-6,10-dioxa-2-azaspiro[4.5]dec-2-yl)-1-cyclopropyl-6-fluoro-4-oxo-1,4-dihydro-3-quinolinecarboxylic acid The compound (4.0 g) obtained from the preparation example 10, 1-cyclopropyl-6,7-difluoro-4-oxo-1,4-dihydro-3-quinoline carboxylic acid (2.9 g) and triethylamine (4.61 ml) were added in acetonitrile (50 ml) in order, and refluxed for 6 hr. Then the precipitate was filtered and dried to obtain the desired compound (5.6 g, 92.9%).

$^1$H-NMR(CDCl$_3$, ppm) 0.80(3H, s), 1.15–1.18(2H, m), 1.20(3H, s), 1.23(3H, s), 1.33(2H, d, J=6.3 Hz) 1.43(9H, s), 3.24(1H, d, J=9.5 Hz), 3.42(2H, d, J=6.1 Hz), 3.49–3.63(6H, m), 3.97–4.01(1H, m), 4.10–4.15(1H, m), 5.17(1H, bs), 6.84(1H, d, J=7.3 Hz), 7.90(1H, d, J=14.2 Hz), 8.63(1H, s)

$[\alpha]_D$=−0.53(c=1, CHCl$_3$, 27.2° C.)

EXAMPLE 4

Preparation of (+)-7-(4-{[(N-t-butoxycarbonyl) amino]methyl}-4,8,8-trimethyl-6,10-dioxa-2-azaspiro[4.5]dec-2-yl)-1-cyclopropyl-6,8-difluoro-4-oxo-1,4-dihydro-3-quinolinecarboxylic acid The compound (1.5 g) obtained from the preparation example 10, 1-cyclopropyl-6,7,8-trifluoro-4-oxo-1,4-dihydro-3-quinolinecarboxylic acid (1.2 g) and triethylamine (0.9 ml) were added in acetonitrile (24 at) in order, and refluxed for 6 hr. Then the precipitate was filtered and dried to obtain the desired compound (2.1 g, 87.6%).

$^1$H-NMR(CDCl$_3$, ppm) 0.78(3H, s), 1.17(5H, s), 1.23(3H, s), 1.26(2H, d, J=7.1 Hz), 1.44(9H, s), 3.39(2H, d, J=5.6 Hz), 3.51~3.61(5H, m), 3.82(1H, bs), 3.96(1H, bs), 4.01(1H, d, J=11.2 Hz), 4.08(1H, d, J=11.2 Hz), 5.13(1H, bs), 7.78–7.85 (1H, m), 8.70(1H, bs)

$[\alpha]_D$=+35.6(c=1, CHCl$_3$, 25.0° C.)

EXAMPLE 5

Preparation of (+)-7-(4-aminomethyl-4-methyl-3-oxopyrrolidin-1-yl)-1-cyclopropyl-6-fluoro-4-oxo-1,4-dihydro[1,8]naphthyridine-3-carboxylic acid hydrochloride The compound (5.31 g) obtained from the example 1 was dissolved in concentrated HCl (25 ml) and stirred at room temperature for 7 hr. Isopropanol (125 ml) was added to the reaction mixture, and stirred for 1 hr. The resulting solid was filtered, washed with isopropanol and dried to give the desired compound (3.78 g, 97.3%).

$^1$H-NMR(DMSO-d$_6$+CF$_3$COOD, ppm) 0.99(2H, bs), 1.18(2H, d, J=8.0 Hz), 1.23(3H, s), 3.05(1H, d, J=13.2 Hz), 3.11(1H, d, J=13.4 Hz) 3.62(1H, m), 4.11(2H, bs), 4.26(1H, d, J=19.0 Hz), 4.46(1H, d, J=22.5 Hz), 7.96(1H, d, J=12.4 Hz), 8.55(1H, s)

$[\alpha]_D$=+12.93(c=1.13, H$_2$O, 25.0° C.)

EXAMPLE 6

Preparation of (−)-5-amino-7-(4-aminomethyl-4-methyl-3-oxopyrrolidin-1-yl)-1-cyclopropyl-6,8-difluoro-4-oxo-1,4-dihydro-3-quinolinecarboxylic acid hydrochloride The compound (3.05 g) obtained from the example 2 was dissolved in concentrated HCl (15 ml) and stirred at room temperature for 7 hr. Isopropanol (125 ml) was added to the reaction mixture, and stirred for 1 hr. The resulting solid was filtered, washed with isopropanol and dried to give the desired compound (2.13 g, 81.1%).

$^1$H-NMR(DMSO-d$_6$+CF$_3$COOD, ppm) 1.04~1.11(4H, m), 1.24(3H, s), 3.02(1H, d, J=13.4 Hz), 3.09(1H, d, J=13.4 Hz) 3.84(1H, d, J=10.7 Hz), 3.91(1H, bs), 4.02(1H, d, J=11.0 Hz), 4.10(1H, d, J=18.5 Hz), 4.17(1H, d, J=18.3 Hz) 8.42(1H, s)

$[\alpha]_D$=−23.64(c=1.41, DMSO, 25° C.)

EXAMPLE 7

Preparation of (−)-7-(4-aminomethyl-4-methyl-3-oxopyrrolidin-1-yl)-1-cyclopropyl-6-fluoro-4-oxo-1,4-dihydro-3-quinolinecarboxylic arid hydrochloride The compound (5.4 g) obtained from the example 3 was dissolved in concentrated HCl (25 ml) and stirred at room temperature for 7 hr. Isopropanol (125 ml) was added to the reaction mixture, and stirred for 1 hr. The resulting solid was filtered, washed with isopropanol and dried to give the desired compound (3.7 g, 89.8%).

$^1$-NMR(DMSO-d$_6$+CF$_3$COOD, ppm) 1.08(2H, s), 1.25 (3H, s), 1.28(2H, s) 3.03~3.12.(2H, m), 3.63(1H, bs), 3.75~3.92(2H, m), 4.07(1H, d, J=15.8 Hz), 4.27(1H, d, J=19.8 Hz), 7.21(1H, d, J=6.8 Hz), 7.84(1H, d, J=14.2 Hz) 8.59(1H, s)

$[\alpha]_D$=−23.64(c=1.41, DMSO, 25.0° C.)

EXAMPLE 8

Preparation of (+)-7-(4-aminomethyl-4-methyl-3-oxopyrrolidin-1-yl)-1-cyclopropyl-6,8-difluoro-4-oxo-1,4-dihydro-3-quinolinecarboxylic acid hydrochloride The compound (1.9 g) obtained from the example 4 was dissolved in concentrated HCl (10 ml) and stirred at room temperature for 7 hr. Isopropanol (50 ml) was added to the reaction mixture, and stirred for 1 hr. The resulting solid was filtered, washed with isopropanol and dried to give the desired compound (1.4 g, 93.7%). $^1$H-NMR(DMSO-d$_6$+CE$_3$COOD, ppm) 1.15(4H, d, J=5.6 Hz), 1.24(3H, s), 3.02 (1H, d, J=13.4 Hz), 3.10(1H, d, J=13.4 Hz), 3.83(1H, d, J=10.7 Hz), 4.12(1H, d, J=18.3 Hz), 4.20(1H, d, J=18.3 Hz), 7.78(1H, d, J=13.2 Hz) 8.64(1H, s)

$[\alpha]_D$=+13.85(c=1, CH$_3$OH, 25.5° C.)

EXAMPLE 9

Preparation of (−)-7-(4-aminomethyl-4-methyl-3-(Z)-methyloxyiminopyrrolidin-1yl)-1-cyclopropyl-6-fluoro-4-oxo-1,4-dihydro[1,8,]naphthyridine-3-carboxylic acid hydrochloride The compound (3.78 g) obtained from the example 5 and methoxylamine hydrochloride (1.62 g) were added in pyridine (40 ml) and stirred for 4 hr. After the reaction mixture was concentrated under reduced pressure, ethyl alcohol (40 ml) was added to the residue, which was stirred for 1 hr. The resulting solid was filtered, washed with acetonitrile and diethyl ether in order, and dried to give the desired compound (3.62 g, 97.5%).

$^1$H-NMR(DMSO-d$_6$+CF$_3$COOD, ppm) 1.05(2H, bs), 1.20(2H, d, J=7.3 Hz), 1.34(3H, s), 3.08(1H, d, J=13.2 Hz) 3.14(1H, d, J=13.2 Hz) 3.15(2H, m), 3.66(1H, bs), 3.86(4H, bs), 4.08(1H, d, J=12.7 Hz), 4.61(2H, s), 8.99(1H, d, J=12.4 Hz), 8.56(1H, s)

$[\alpha]_D$=−1.5(c=1.2, CH$_3$OH, 27.6° C.)

EXAMPLE 10

Preparation of (+)-7-(4-aminomethyl-4-methyl-3-(Z)-ethyloxyiminopyrrolidine-1-yl)-1-cyclopropyl-6-fluoro-4-oxo-1,4-dihydro[1,8]naphthyridine-3-carboxylic acid hydrochloride The compound (300 mg) obtained from the example 5 and ethylhydroxylamine hydrochloride (142 mg) were added in pyridine (10 ml) and stirred at 60° C. for 7 hr. After the reaction mixture was concentrated under reduced pressure, diethyl ether (10 ml) was added, which was stirred for 1 hr. The resulting solid was filtered, washed with acetonitrile and diethyl ether in order, and dried to give the desired compound (258 mg, 50.3%).

$^1$H-NMR(DMSO-d$_6$+CF$_3$COOD, ppm) 1.07(2H, bs), 1.20–1.23(5H, m), 1.35(3H, s), 3.10–3.13(2H, m), 3.69(1H, bs), 3.88(1H, bs), 4.10–4.14(3H, m), 4.62(2H, bs), 8.01(1H, d, J=12.7 Hz), 8.57(1H, s)

$[\alpha]_D$=+3.98(c=1, CH$_3$OH, 23.2° C.)

EXAMPLE 11

Preparation of (+)-7-(4-aminomethyl-4-methyl-3-(Z)-t-buthyloxyiminopyrrolidin-1-yl)-1-cyclopropyl-6-fluoro-4-oxo-1,4-dihydro[1,8]naphthyridine-3-carboxylic acid hydrochloride The compound (300 mg) obtained from the example 5 and t-butylhydroxylamine hydrochloride (183 mg) were added in pyridine (10 ml). After the reaction mixture was stirred at 60° C. for 7 hr, which was concentrated under reduced pressure. Diethyl ether (10 ml) was added to the reaction mixture, which was stirred for 1 hr. The resulting solid was filtered, washed with acetonitrile and diethyl ether in order, and dried to give the desired compound (200 mg, 52.9%).

$^1$H-NMR(DMSO-d$_6$+CF$_3$COOD, ppm) 1.07–1.12(2H, m), 1.21–1.22(2H, m), 1.26(9H, s), 1.35(3H, s), 3.06(1H, d, J=13.2 Hz), 3.15(1H, d, J=13.2 Hz), 3.68(1H, bs), 3.89(1H, d, J=13.2 Hz), 4.07(1H, d, J=11.9 Hz), 4.59(2H, s), 8.03 (1H, d, J=8.8 Hz), 8.56(1H, s)

$[\alpha]_D$=+9.71(c=1, CH$_3$OH, 20.7° C.)

EXAMPLE 12

Preparation of (+)-7-(4-aminomethyl-4-methyl-3-(Z)-benzyloxyiminopyrrolidin-1-yl)-1-cyclopropyl-6-fluoro-4-oxo-1,4-dihydro[1,8]naphthyridine-3-carboxylic acid hydrochloride The compound (300 mg) obtained from the example 5 and benzylhydroxylamine hydrochloride (198 mg) were added in pyridine (10 ml). After the reaction mixture was stirred at 60° C. for 7 hr, which was concentrated under reduced pressure. Diethyl ether (10 ml) was added to the reaction mixture, which was stirred for 1 hr. The resulting solid was filtered, washed with acetonitrile and diethyl ether in order, and dried to give the desired compound (150 mg, 40.0%).

$^1$H-NMR(DMSO-d$_6$+CF$_3$COOD, ppm) 1.05–1.10(2H, m), 1.19(2H, d, J=7.1 Hz), 1.34(3H, s), 3.08(1H, d, J=13.2 Hz), 3.14(1H, d, J=13.2 Hz), 3.68(1H, bs) 3.89(1H, d, J=12.43 Hz), 4.09(1H, d, J=11.47 Hz), 4.68(2H, s), 5.16(2H, s), 7.27–7.38(5H, m), 8.02(1H, d, J=12.4 Hz), 8.57(1H, s)

$[\alpha]_D$=+14.75(c=1, CH$_3$OH, 23.8° C.)

EXAMPLE 13

Preparation of (+)-7-(4-aminomethyl-4-methyl-3-(Z)-allyloxyiminopyrrolidin-1-yl)-1-cyclopropyl-6-fluoro-4-oxo-1,4-dihydro[1,8]naphthyridine-3-carboxylic acid hydrochloride The compound (300 mg) obtained from the example 5 and allylhydroxylamine hydrochloride (134 mg) were added in pyridine (10 ml). After the reaction mixture was stirred at 60° C. for 7 hr, which was concentrated under reduced pressure. acetonitrile (10 ml) was added to the reaction mixture, which was stirred for 1hr. The resulting solid was filtered, washed with acetonitrile and diethyl ether in order, and dried to give the desired compound (290 mg, 79.4%).

$^1$H-NMR(DMSO-d$_6$+CF$_3$COOD, ppm) 1.05(2H, bs), 1.20(2H, d, J=7.1 Hz), 1.35(3H, s), 3.07(1H, d, J=13.2 Hz), 3.14(1H, d, J=13.2 Hz), 3.67(1H, bs), 3.88(1H, d, J=12.0 Hz) 4.08(1H, bs), 4.60–4.64(4H, m), 5.17(1H, d, J=10.5 Hz), 5.28(1H, d, J=17.3 Hz), 5.92–6.01(1H, m), 7.97(1H, d, J=12.5 Hz), 8.54(1H, s)

$[\alpha]_D$=+7.98(C=1, CH$_3$OH, 25.6° C.)

EXAMPLE 14

Preparation of (−)-5-amino-7-(4-aminomethyl-4-methyl-3-(Z)-methyloxyiminopyrrolidin-1-yl)-1-cyclopropyl-6,8-difluoro-4-oxo-1,4-dihydro-3-quinolinecarboxylic acid hydrochloride The compound (2.13 g) obtained from the example 6 and methoxylamine hydrochloride (1.20 g) were added in pyridine (20 ml). After the reaction mixture was stirred at 70° C. for 4 hr, which was cooled at room temperature. Isopropyl alcohol (20 ml) was added to the reaction mixture, which was stirred for 1 hr. The resulting solid was filtered, washed with acetonitrile and diethyl ether in order, and dried to give the desired compound (1.98 g, 94.5%).

$^1$H-NMR(DMSO-d$_6$+CF$_3$COOD, ppm) 0.98(2H, bs), 1.03(2H, d, J=6.8 Hz), 1.28(3H, s), 3.00(1H, d, J=13.2 Hz), 3.05(1H, d, J=13.2 Hz), 3.59(1H, d, J=10.8 Hz), 3.79(4H, bs), 3.91(1H, bs), 4.25(1H, d, J=17.3 Hz), 4.41(1H, d, J=17.3 Hz), 8.45(1H, s)

$[\alpha]_D$=−1.2(c=1.0, CH$_3$OH, 27.7° C.)

EXAMPLE 15

Preparation of (−)-5-amino-7-(4-aminomethyl-4-methyl-3-(Z)-ethyloxyiminopyrrolidin-1-yl)-1-cyclopropyl-6,8-difluoro-4-oxo-1,4-dihydro-3-quinolinecarboxylic acid hydrochloride The compound (200 mg) obtained from the example 6 and ethylhydroxylamine hydrochloride (66 mg) were added in pyridine (10 ml). After the reaction mixture was stirred at 60° C. for 7 hr, which was concentrated under reduced pressure. Acetonitrile (10 ml) was added to the residue, which was stirred for 1 hr more. The resulting solid was filtered, washed with acetonitrile and diethyl ether in order, and dried to give the desired compound (165 mg, 75.2%).

$^1$H-NMR(CD$_3$OD, ppm) 1.12–1.20(4H, m), 1.28(3H, t, J=7.1 Hz), 1.30(3H, s), 3.02(1H, d, J=13.2 Hz), 3.08(1H, d, J=13.2 Hz), 3.64(1H, d, J=10.7 Hz), 3.84(1H, d, J=10.5 Hz), 3.96(1H, bs), 4.03–4.09(2H, m), 4.30(1H, d, J=17.3 Hz), 4.43(1H, d, J=17.3 Hz), 8.48(1H, s)

$[\alpha]_D$=−24.69 (c=1, CH$_3$OH, 23.1° C.)

EXAMPLE 16

Preparation of (−)-5-amino-7-(4-aminomethyl-4-methyl-3-(Z)-t-butyloxyiminopyrrolidin-1-yl)-1-cyclopropyl-6,8-difluoro-4-oxo-1,4-dihydro-3-quinolinecarboxylic acid hydrochloride The compound (300 mg) obtained from the example 6 and t-butylhydroxylamine hydrochloride (170 mg) were added in pyridine (10 ml). After the reaction mixture was stirred at 70° C. for 7 hr, which was cooled at room temperature. Diethyl ether (10 ml) was added to the reaction mixture, which was stirred for 1 hr more. The resulting solid was filtered, washed with acetonitrile and diethyl ether in order, and dried to give the desired compound (181 mg, 49.5%).

1H-NMR(DMSO-d$_6$+CF$_3$COOD, ppm) 1.05–1.09(4H, m), 1.23(9H, s), 1.31(3H, s), 3.00(1H, d, J=13.2 Hz), 3.08 (1H, d, J=13.2 Hz), 3.64(1H, d, J=10.5 Hz), 3.84(1H, d, J=10.5 Hz), 3.96(1H, bs), 4.26(1H, d, J=17.3 Hz), 4.39(1H, d, J=17.3 Hz), 8.46(1H, s)

$[\alpha]_D$=−22.23(c=1, CH$_3$OH, 20.4° C.)

EXAMPLE 17

Preparation of (−)-5-amino-7-(4-aminomethyl-4-methyl-3-(Z)-benzyloxyiminopyrrolidin-1-yl)-1-cyclopropyl-6,8-difluoro-4-oxo-1,4-dihydro-3-quinolinecarboxylic acid hydrochloride The compound (300 mg) obtained from the example 6 and benzylhydroxylamine hydrochloride (162 mg) were added in pyridine (10 ml). After the reaction mixture was stirred at 70° C. for 7 hr, which was cooled at room temperature. Acetonitrile (10 ml) was added to the reaction mixture, which was stirred for 1 hr more. The resulting solid was filtered, washed with acetonitrile and diethyl ether in order, and dried to give the desired compound (280 mg, 75.4%).

$^1$H-NMR(DMSO-d$_6$+CF$_3$COOD, ppm) 1.04–1.07(4H, m), 1.30(3H, s), 3.01(1H, d, J=13.2 Hz), 3.09(1H, d, J=13.2 Hz), 3.65(1H, d, J=10.5 Hz), 3.85(1H, d, J=10.5 Hz), 3.93(1H, bs), 4.34(1H, d, J=17.32 Hz), 4.47(1H, d, J=17.3 Hz), 5.12(2H, s), 7.28–7.36(5H, m), 8.47(1H, s)

$[\alpha]_D$=−4.25(c=1, CH$_3$OH, 28.2° C.)

EXAMPLE 18

Preparation of (−)-5-amino-1-(4-aminomethyl-4-methyl-3-(Z)-allyloxyiminopyrrolidin-1-yl)-1-cyclopropyl-6,8-difluoro-4-oxo-1,4-dihydro-3-quinolinecarboxylic acid hydrochloride The compound (500 mg) obtained from the example 6 and allylhydroxylamine hydrochloride (186 mg) were added in pyridine (10 ml). After the reaction mixture was stirred at 70° C. for 4 hr, which was cooled at room temperature. Acetonitrile (10 ml) was added to the reaction mixture, which was stirred for 1 hr more. The resulting solid was filtered, washed with acetonitrile and diethyl ether in order, and dried to give the desired compound (445 mg, 79.2%).

$^1$H-NMR(DMSO-d$_6$+CF$_3$COOD, ppm) 1.02–1.09(4H, m), 1.30(3H, s), 3.01(1H, d, J=13.2 Hz), 3.09(1H, d, J=13.2 Hz), 3.64(1H, d, J=10.5 Hz), 3.84(1H, d, J=10.5 Hz), 3.95(1H, bs), 4.33(1H, d, J=17.3 Hz), 4.46(1H, d, J=17.3 Hz), 4.57(2H, d, J=5.40 Hz), 5.16(1H, d, J=10.5 Hz), 5.25(1H, d, J=19.04 Hz,), 5.91–6.00(1H, m), 8.47(1H, s)

$[\alpha]_0$=−24.54(c=1, CH$_3$OH, 22.1° C.)

EXAMPLE 19

Preparation of (−)-7-(4-aminomethyl-4-methyl-(Z)-methyloxyiminopyrrolidin-1-yl)-1-cyclopropyl-6-fluoro-4-oxo-1,4-dihydro-3-quinolinecarboxylic acid hydrochloride The compound (300 mg) obtained from the example 7 and methoxylamine hydrochloride (92 mg) were added in pyridine (10 ml). After the reaction mixture was stirred at 50° C. for 7 hr, which was concentrated under reduced pressure. Acetonitrile (10 ml) was added to the reaction mixture, which was stirred for 1 hr more. The resulting solid was filtered, washed with acetonitrile and diethyl ether in order, and dried to give the desired compound (265 mg, 80.4%).

$^1$H-NMR(DMSO-d$_6$+CF$_3$COOD, ppm) 1.14(2H, bs), 1.31(2H, bs), 1.36(3H, s), 3.09–3.15(2H, m), 3.61(1H, bs), 3.74(1H, bs), 3.86(4H, s), 4.44(2H, s), 7.21(1H, s), 7.84(1H, d, J=14.15 Hz), 8.59(1H, s)

$[\alpha]_D$=−16.5(c=1, CH$_3$OH, 22.8° C.)

EXAMPLE 20

Preparation of (+)-7-(4-aminomethyl-4-methyl-3-(Z)-ethyloxyiminopyrrolidin-1-yl)-1-cyclopropyl-6-fluoro-4-oxo-1,4-dihydro-3-quinolinecarboxylic acid hydrochloride The compound (300 mg) obtained from the example 7 and ethylhydroxylamine hydrochloride (107 mg) were added in pyridine (10 ml). After the reaction mixture was stirred at 50° C. for 4 hr, which was concentrated under reduced pressure. Acetonitrile (10 ml) was added to the reaction mixture, which was stirred for 1 hr more. The resulting solid was filtered, washed with acetonitrile and diethyl ether in order, and dried to give the desired compound (235 mg, 71.3%).

$^1$H-NMR(DMSO-d$_6$+CF$_3$COOD, ppm) 1.13–1.15(2H, m), 1.21(3H, t, J=6.95 Hz ), 1.28–1.39(5H, m), 3.07(1H, d, J=13.0 Hz), 3.14(1H, d, J=13.0 Hz), 3.58(1H, d, J=10.5 Hz) 3.72(1H, bs), 3.86(1H, d, J=10.6 Hz), 4.12(2H, q, J=7.1 Hz), 4.44(2H, s), 7.19(1H, d, J=7.55 Hz), 7.79(1H, d, J=13.9 Hz), 8.53(1H, s)

[α]$_D$=+23.68(c=1, CH$_3$OH, 23.3° C.)

EXAMPLE 21

Preparation of (−)-7-(4-aminomethyl-4-methyl-3-(Z)-t-butyloxyiminopyrrolidin-1-yl)-1-cyclopropyl-6-fluoro-4-oxo-1,4-dihydro-3-quinolinecarboxylic acid hydrochloride The compound (300 mg) obtained from the example 7 and t-butylhydroxylamine hydrochloride (183 mg) were added in pyridine (10 ml). After the reaction mixture was stirred at 60° C. for 7 hr, which was cooled at room temperature. Diethyl ether (10 ml) was added to the reaction mixture, which was stirred for 1 hr more. The resulting solid was filtered, washed with acetonitrile and diethyl ether in order, and dried to give the desired compound (245 mg, 69.7%).

$^1$H-NMR(DMSO-d$_6$+CF$_3$COOD, ppm) 1.08–1.14(2H, m), 1.24(9H, s), 1.28–1.34(2H, m), 1.36(3H, s), 3.05(1H, d, J=13.2 Hz), 3.14(1H, d, J=13.2 Hz), 3.56(1H, d, J=10.8 Hz), 3.69(1H, bs), 3.84(1H, d, J=13.2 Hz), 4.35–4.45(2H, m), 7.17(1H, d, J=7.6 Hz), 7 80(1H, d, J=10.0 Hz), 8.52(1H, s)

[α]$_D$=−7.05(c=1, CH$_3$OH, 21.6° C.)

EXAMPLE 22

Preparation of (+)-7-(4-aminomethyl-4-methyl-3-(Z)-benzyloxyiminopyrrolidin-1-yl)-1-cyclopropyl-6-fluoro-4-oxo-1,4-dihydro-3-quinolinecarboxylic acid hydrochloride The compound (300 mg) obtained from the example 7 and benzylhydroxylamine hydrochloride (197 mg) were added in pyridine (10 ml). After the reaction mixture was stirred at 50° C. for 7 hr, which was concentrated under reduced pressure. Acetonitrile (10 ml) was added to the residue, which was stirred for 1 hr more. The resulting solid was filtered, washed with acetonitrile and diethyl ether in order, and dried to give the desired compound (237 mg, 64.7%).

$^1$H-NMR (DMSO-d$_6$+CF$_3$COOD, ppm) 1.12(2H, bs), 1.33(2H, bs), 1.36(3H, s), 3.07(1H, d, J=13.2 Hz), 3.15(1H, d, J=13.2 Hz), 3.58(1H, d, J=10.5 Hz), 3.70(1H, bs), 3.87 (1H, d, J=10.8 Hz), 4.50(2H, bs), 5.15(2H, s), 7.19(1H, d, J=7.5 Hz), 7.26–7.38(5H, m), 7.78(1H, d, J=13.9 Hz), 8.52(1H, s)

[α]$_D$=+7.47(c=1, CH$_3$OH, 23.7° C.)

EXAMPLE 23

Preparation of (−)-7-(4-aminomethyl-4-methyl-3-(Z)-methyloxyiminopyrrolidin-1-yl)-1-cyclopropyl-6,8-difluoro-4-oxo-1,4-dihydro-3-quinolinecarboxylic acid hydrochloride The compound, (300 mg) obtained from the example 8 and methoxylamine hydrochloride (117 mg) were added in pyridine (10 ml). After the reaction mixture was stirred at 60° C. for 8 hr, which was concentrated under reduced pressure. Acetonitrile (10 ml) was added to the residue, which was stirred for 1 hr more. The resulting solid was filtered, washed with acetonitrile and diethyl ether in order, and dried to give the desired compound (210 mg, 65.1%).

$^1$H-NMR(DMSO-d$_6$+CF$_3$COOD, ppm) 1.23 (4H, bs), 1.30(3H, s), 3.02(1H, d, J=13.1 Hz), 3.07(1H, d, J=13.1 Hz), 3.64(1H, d, J=10.5 Hz), 3.80–3.86(4H, m), 4.00(1H, bs), 4.301(1H, d, J=17.3 Hz), 4.64(1H, d, J=17.3 Hz), 7.70(1H, d, J=13.2 Hz), 8.59(1H, s)

[α]$_D$=−20.98(c=1, CH$_3$OH, 21.7° C.)

Experimental Example 1

Antibacterial Activity In Vitro

The optically active quinoline carboxylic acid derivatives of the present invention were tested as to whether they could be useful as antibacterial compounds. In this regard, the compounds were measured for minimum inhibitory concentration (MIC: unit μg/ml) according to an agar dilution process (Hoechst 345) in which Muller-Hinton agars were diluted two fold. For comparison, ciprofloxacin and sparfloxacin were used as controls. Corresponding enantiomers and racemates of the compounds of interest were also used as comparative ones. Bacteria were inoculated at an amount of about 10$^7$ cfu/ml onto each agar. 18 hours after the inoculation at 37° C., the growth of the bacteria was observed. As to methicillin-resistant strains, their growth was observed 48 hours after the inoculation at 30° C. Hoechst standard strains were used as the test bacteria. The result were shown in Table 1 and Table 2.

TABLE 1

Antibacterial Activity In Vitro (μg/ml)

| Strain | Example 9 | Example 14 | Example 19 | Ciprofloxacin | Sparfloxacin |
|---|---|---|---|---|---|
| Standard strain | | | | | |
| Streptococus pyogenes 308A | 0.025 | 0.004 | 0.049 | 3.125 | 0.391 |
| Streptococus pyogenes 77A | 0.013 | <0.002 | 0.013 | 0.391 | 0.391 |
| Streptococus faecium MD 8b | 0.049 | 0.013 | 0.049 | 0.391 | 0.391 |
| Staphylococcus aureus SG511 | 0.004 | <0.002 | 0.004 | 0.195 | 0.098 |
| Staphylococcus aureus 285 | 0.007 | <0.002 | 0.007 | 0.781 | 0.049 |
| Staphylococcus aureus 503 | 0.004 | <0.002 | 0.007 | 0.391 | 0.049 |
| Escherichia coli DC 0 | 0.004 | 0.004 | 0.007 | 0.195 | 0.195 |
| Escherichia coli DC 2 | 0.195 | <0.002 | 0.195 | 0.098 | 0.025 |
| Pseudomonas aeruginosa 1771M | 0.391 | 0.195 | 0.195 | 0.098 | 0.098 |
| Enterobacter cloacae P99 | 0.025 | <0.002 | 0.025 | 0.013 | 0.007 |
| Staphylococcus aureus 88E | <0.002 | <0.002 | 0.007 | 0.781 | 0.098 |
| Staphylococcus aureus 121E | <0.002 | <0.002 | 0.007 | 0.781 | 0.098 |
| Staphylococcus aureus 208E | <0.002 | <0.002 | 0.007 | 0.781 | 0.096 |
| Staphylococcus aureus 256E | <0.002 | <0.002 | 0.007 | 0.781 | 0.098 |
| Staphylococcus aureus 690E | <0.002 | <0.002 | 0.004 | 0.391 | 0.049 |

TABLE 1-continued

Antibacterial Activity In Vitro (μg/ml)

| Strain | Example 9 | Example 14 | Example 19 | Cipro-floxacin | Spar-floxacin |
|---|---|---|---|---|---|
| Staphylococcus aureus 692E | <0.002 | <0.002 | 0.004 | 0.391 | 0.049 |
| Staphylococcus aureus 693E | <0.002 | <0.002 | 0.007 | 0.391 | 0.049 |
| Staphylococcus aureus 179 | 0.098 | 0.013 | 0.195 | 12.500 | 6.250 |
| Staphylococcus aureus 241 | 0.096 | 0.013 | 0.195 | 12.500 | 6.250 |
| Staphylococcus aureus 293 | 0.096 | 0.013 | 0.195 | 12.500 | 6.250 |
| Staphylococcus aureus 303 | 0.098 | 0.013 | 0.195 | 12.500 | 3.125 |
| Staphylococcus epidermidis 319 | 0.195 | 0.025 | 0.391 | 100.00 | 12.500 |
| Staphylococcus epidermidis 329 | 0.195 | 0.025 | 0.391 | 50.000 | 12.500 |

As may be seen from the data of Table 1, the compounds prepared in Examples 9, 14 and 19 are far superior in antibacterial activity to ciprofloxacin and sparfloxacin, representatives of conventional quinolone antibacterial agents.

In quantitative analysis, the compound of Example 9 showed 4–112 fold higher antibacterial activity against Gram-positive bacteria than ciprofloxacin, and 4–30 fold higher than sparfloxacin. Escherichia coli, a representative Gram-negative strain, underwent almost the same antibacterial potency from the compound of Example 9 and from ciprofloxacin and sparfloxacin. Especially, against Staphylococcus aureus and Staphylococcus epidermis, both resistant to quinolone antibacterial agents, the compound of Example 9 was 128–390 times as potent in antibacterial activity as ciprofloxacin was and 24–64 times as potent as sparfloxacin was Also, the compound of Example 14 showed 30–781 fold higher antibacterial activity against Gram-positive bacteria than ciprofloxacin and 24–195 fold higher than sparfloxacin. Against Escherichia coli, a representative Gram-negative strain, the compound, of Example 14 exerted 49 fold more potent antibacterial effect than ciprofloxacin, and 12–49 fold more than sparfloxacin. Especially, against the resistant strains of Staphylococcus aureus and Staphylococcus epidermis, the compound of Example 14 was 129–962 times as potent in antibacterial activity as ciprofloxacin was and 24–481 times as potent as sparfloxacin was.

With far superiority in antibacterial activity against the Grain-positive bacteria and the resistant strains to ciprofloxacin and sparfloxacin, the compound of Example 19 exhibited similar antibacterial behaviors against all the Gram-positive bacteria, the Gram-negative bacteria, and the resistant strains of Staphylococcus aureus and Staphylococcus epidermis to those that the compounds of Examples 9 and 14 did. The compound of example 19 also showed superior antibacterial activity against the Gram-negative bacteria to ciprofloxacin and sparfloxacin.

TABLE 2

Antibacterial Activity In Vitro (μg/ml)

| Resistant strain | Compound of Example 9 | Racemate of Example 9 Compound | Enantiomer of Example 9 Compound | Compound of Example 14 | Racemate of Example 14 Compound | Enantiomer of Example 14 Compound | Compound of Example 19 | Racemate of Example 19 Compound | Enantiomer of Example 19 Compound |
|---|---|---|---|---|---|---|---|---|---|
| Staphylococcus aureus 88E | <0.002 | 0.007 | 0.025 | <0.002 | <0.002 | 0.007 | 0.007 | 0.013 | 0.098 |
| Staphylococcus aureus 121 E | <0.002 | 0.007 | 0.049 | <0.002 | <0.002 | 0.013 | 0.007 | 0.013 | 0.098 |
| Staphylococcus aureus 208E | <0.002 | 0.007 | 0.049 | <0.002 | <0.002 | 0.013 | 0.007 | 0.013 | 0.098 |
| Staphylococcus aureus 256E | <0.002 | 0.007 | 0.025 | <0.002 | <0.002 | 0.013 | 0.007 | 0.013 | 0.098 |
| Staphylococcus aureus 690E | <0.002 | 0.004 | 0.025 | <0.002 | <0.002 | 0.004 | 0.004 | 0.007 | 0.049 |
| Staphylococcus aureus 692E | <0.002 | <0.002 | 0.025 | <0.002 | <0.002 | 0.004 | 0.004 | 0.013 | 0.049 |
| Staphylococcus aureus 693E | <0.002 | 0.007 | 0.025 | <0.002 | 0.002 | 0.004 | 0.007 | 0.013 | 0.098 |
| Staphylococcus aureus 179 | 0.098 | 0.195 | 1.563 | 0.013 | 0.025 | 0.195 | 0.195 | 0.391 | 3.125 |
| Staphylococcus aureus 241 | 0.098 | 0.195 | 1.563 | 0.013 | 0.025 | 0.195 | 0.195 | 0.391 | 3.125 |
| Staphylococcus aureus 293 | 0.098 | 0.195 | 1.563 | 0.013 | 0.025 | 0.195 | 0.195 | 0.391 | 3.125 |
| Staphylococcus aureus 303 | 0.098 | 0.195 | 0.781 | 0.013 | 0.025 | 0.195 | 0.195 | 0.391 | 3.125 |
| Staphylococcus epidermidis 319 | 0.391 | 0.391 | 6.250 | 0.025 | 0.049 | 0.781 | 0.391 | 0.781 | 12.500 |
| Staphylococcus epidermidis 329 | 0.391 | 0.781 | 12.500 | 0.025 | 0.098 | 1.563 | 0.391 | 0.781 | 12.500 |

Table 2 shows that the compounds of Examples 9, 14 and 19 possess far more potent antibacterial activity against the resistant *Staphylococcus aureus* and *Staphylococcus epidermis* than those that corresponding racemates and enantiomers do.

Quantitatively, the compound of example 9 has 4 fold more potent antibacterial activity than its racemate and 8–32 fold than its enantiomer against *staphylococcus aureus* and *staphylococcus epidermis*.

The compound of Example 14 was up to four fold more potent than its racemate and 2–63 fold more than its enantiomer. Two fold higher potency and 12–32 fold higher potency in the antibacterial activity were measured from the compound of Example 19 than from its racemate and enantiomer, respectively.

Taken together, the data obtained in the above examples exhibit that the compounds of the present invention possess better antibacterial activity than not only conventional quinolone antibacterial agents, but also their respective racemates and enantiomers.

Experimental Example 2

Pharmacokinetic Test

The pharmacokinetic profiles of the optically active compounds of the present invention were examined as to whether they could be applied as useful drugs to the body. Ciprofloxacin was used as control.

After being starved for 16 hours, SD rats were orally administered at a dose of 40 mg/5 ml/kg with the compounds of interest and at a dose of 50 mg/5 ml/kg with the control. Immediately after being drawn at predetermined times from the eyeballs, blood was separated into plasma and other ingredients and quantitatively analyzed for pharmacokinetic parameters by use of high performance liquid chromatograph (HPLC).

TABLE 3

Pharmacokinetic test

| | Compound of example 9 | Compound of example 14 | Ciprofloxacin |
|---|---|---|---|
| Maximal concentration in Blood $C_{max}$ (µg/ml) | 9.06 ± 2.040 | 6.67 ± 3.327 | 4.39 ± 1.220 |
| Time of Maximal concentration | 2.00 | 1.00 | 0.50 |
| Half life period [$t_{1/2}$(hr)] | 4.50 | 6.94 | 2.07 |
| Area Under Curve (µg.hr/ml) | 90.82 | 68.77 | 12.72 |

As indicated in Table 3, both the compounds of Examples 9 and 14 have excellent advantages in maximal concentration in blood [$C_{max}$(µg /ml)], half life period [$t_{1/2}$(hr)], area under curve [AUC (µg.hr/ml)] over ciprofloxacin, a representative quinolone antibacterial agent.

Therefore, the data of Table 3 demonstrate that in vivo pharmacokinetic properties of the optically active quinoline carboxylic acid derivatives represented by the formula 1 are greatly improved compared with those of conventional quinolone antibacterial agents.

Experimental Example 3

Phototoxicity Test

It is known that the presence of a halogen atom at the 8-position of the quinolone nuclei causes phototoxicity. Thus, the compound prepared in Example 14 was examined as to whether it would show phtotoxicity. For comparison, sparfloxacin, the (+)-form enantiomer of the compound of Example 14, and its racemate were used as controls. As a negative control, mice which had been administered with no agents were used.

After 16 hours of starvation, CD-1 female mice were orally administered with a dose of 50 mg/kg of the compounds and allowed to be exposed for 4.5 hours to a UVA light source. The mice were located 15 cm away from the light source. Whether the mice were damaged in their, ears was adopted as a main factor for the phototoxicity and determined after 24 hour and 48 hour UV exposure. The edema which the mice suffered were examined by measuring the thickness changes of their ears with the aid of electronic calipers and calculating average values. Also, an observation was made as to whether the mice suffered from erythema.

TABLE 4

Thickness changes of mice's ears after UV exposure

| | Dosage (mg/kg) | Thickness of mice's ears after UV exposure | | |
|---|---|---|---|---|
| | | Before UV exposure | After 24 hr | After 48 hr |
| Negative control group | 0 | 18.1 ± 1.13 | 20.0 ± 0.76 | 20.5 ± 0.76 |
| Compound of Example 14 | 50 | 18.5 ± 0.76 | 21.6 ± 0.52 | 21.6 ± 0.52 |
| Racemic mixture of Example 14 compound | 50 | 17.6 ± 0.52 | 23.5 ± 1.31 | 24.4 ± 2.33 |
| Enantiomer of Example 14 compound | 50 | 17.8 ± 0.89 | 36.3 ± 3.01 | 44.5 ± 4.0 |
| Ciprofloxacin (Positive control group) | 50 | 18.1 ± 0.64 | 38.0 ± 2.73 | 46.0 ± 4.31 |

After 48 hours of the UV exposure, the mice which had been, administered with the racemate of the compound of Example 14 suffered from moderate edema and erythema with an increase in ear thickness by 39% compared with before the UV exposure. When exposed to the UVA light source during the same period, the mice which had been administered with the enantiomer of the compound of Example 14 or with sparfloxacin suffered from serious edema and erythema with an increase in ear thickness by as much as 150% compared with before the UV exposure. In contrast, no erythema was observed in the mice which had been administered with the compound of Example 14. Their ears were measured to be increased by 16.8% compared with before the exposure. However, when the standard deviation was taken into account, the increase extent was said to be not different from 13.2% the negative control group exhibited.

Consequently, the optically active quinoline carboxylic acid derivative of Example 14, although containing a halogen atom at the 8-position of the quinolone nuclei, hardly causes phototoxicity on the contrary to conventional compounds.

Industrial Applicability

The optically active quinoline carboxylic acid derivatives, represented by the formula 1, in more detail, the optically active quinoline carboxylic acid derivatives, which possess optical activity-causing 4-aminomethyl-4-methyl-3-(Z)- alkoxyiminopyrrolidine substituents at the 7-position of the quinolone nuclei, show surprisingly improved antibacterial activity against Gram-positive bacteria, which have been difficult for conventional agents to conquer, in addition to still possessing excellent antibacterial activity against Gram-negative bacteria. Particularly, the optically active quinoline carboxylic acid derivatives of the present invention exert superior control effects on the strains resistant to methicillin and conventional quinolone agents. In addition, because the compounds of the formula 1 are far more potent in antibacterial activity than corresponding racemates and enantiomers, identical or greater in vivo efficacy can be obtained from the compounds of the formula 1 even if their doses are smaller. Therefore, the compounds of the invention impose smaller loads on the body.

As demonstrated above, the compounds of the present invention are superior to conventional quinolone antibacterial agents in pharmacokinetic properties, including maximal concentration in blood, half life period, and area under curve. With such excellent antibacterial activity and pharmacokinetic profiles, the compounds of the present invention enjoy the advantage of being administered at a dose 2–4 fold lesser than conventional quinolone antibacterial agents, corresponding racemates or other enantiomers.

Further, the optically active quinoline carboxylic acid derivatives of the present invention, even if possessing a hologen atom (e.g., fluorine atom) at the 8-position of the quinolone nuclei, exhibit nearly no phototoxicity.

In conclusion, the optically active quinoline carboxylic acid derivatives represented by the formula 1 possess highly potent antibacterial activity with remarkably low toxicity and are very suitable for use in the prophylaxis or treatment of bacteria-caused diseases on humans and animals, substituting for their racemates and other enantiomers.

What is claimed is:

1. An optically active quinoline carboxylic acid derivative represented by the following formula 1, containing optical activity-causing 4-aminomethyl-4-methyl-3-(Z)-alkoxyiminopyrrolidine substituents at the 7-position of the quinolone nuclei, or its pharmaceutically acceptable salt,

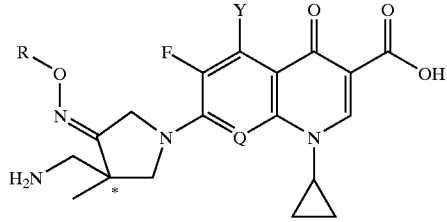

Formula 1 wherein,
Q is N;
Y is H or $NH_2$;
R is a straight or branched alkyl group of $C_1$–$C_4$, an allyl group or a benzyl group, and
* represents optically pure chiral carbon atom.

2. The optically active quinoline carboxylic acid derivative, or its pharmaceutically acceptable salt according to claim 1, wherein Q is N; Y is H or $NH_2$; and R is an alkyl group of $C_1$–$C_2$ or an allyl group.

3. A process for preparing an optically active quinoline carboxylic acid derivative of claim 1 comprises the steps:

a) condensing the quinolone nuclei-containing compound of formula 3

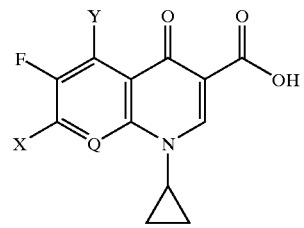

3 with the ketal compound of formula 2a

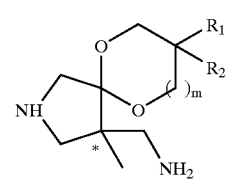

2a in the presence of an acid acceptor to give the optically active quinoline carboxylic acid derivative of formula 4;

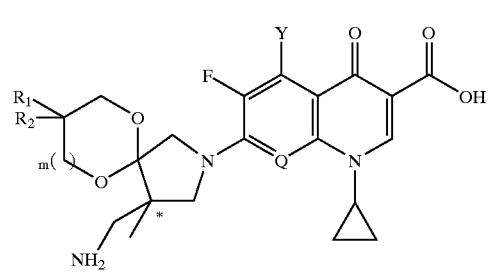

4 b) deketalizing the optically active quinoline carboxylic acid derivative of formula 4 to give the pyrrolidinone compound of formula 5

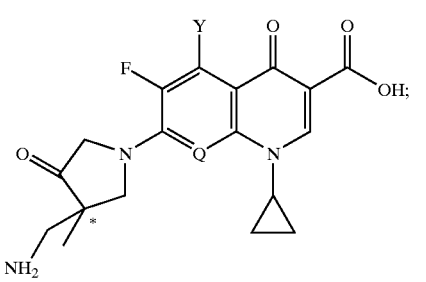

5 and c) reacting the pyrrolidinone compound of formula 5 with an alkoxylamine in the presence of a base to obtain the desired compound of formula 1

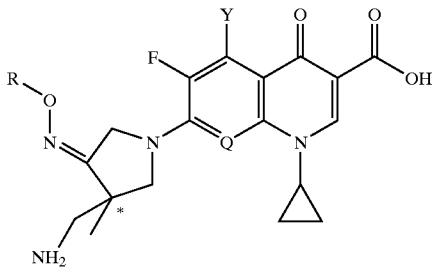

wherein,
Q is N;
Y is H or NH$_2$;

R is a straight or branched alkyl group of $C_1$–$C_4$, an allyl group or a benzyl group,
* represents optically pure chiral carbon atom,
X is a halogen atom,
R$_1$ and R$_2$ are H or methyl,
R$_1$ and R$_2$ are the same; and
m is 0 or 1.

4. The process for preparing the optically active quinoline carboxylic acid derivative of claim 3, wherein X is a fluorine atom.

5. The process for preparing the optically active quinoline carboxylic acid derivative of claim 3, wherein X is a chlorine atom.

* * * * *